(12) United States Patent
Shan

(10) Patent No.: US 12,194,170 B2
(45) Date of Patent: Jan. 14, 2025

(54) GERMICIDAL LIGHTING SYSTEM

(71) Applicant: LED SMART INC., Surrey (CA)

(72) Inventor: Xinxin Shan, Surrey (CA)

(73) Assignee: LED Smart Inc., Surrey (CA)

( * ) Notice: Subject to any disclaimer, the term of this patent is extended or adjusted under 35 U.S.C. 154(b) by 740 days.

(21) Appl. No.: 17/313,983

(22) Filed: May 6, 2021

(65) Prior Publication Data

US 2021/0346547 A1 Nov. 11, 2021

Related U.S. Application Data

(60) Provisional application No. 63/020,983, filed on May 6, 2020.

(30) Foreign Application Priority Data

Jun. 11, 2020 (CA) ..................................... 3083292

(51) Int. Cl.
*A61L 2/10* (2006.01)

(52) U.S. Cl.
CPC ............ *A61L 2/10* (2013.01); *A61L 2202/11* (2013.01); *A61L 2202/14* (2013.01); *A61L 2202/16* (2013.01)

(58) Field of Classification Search
CPC .... A61L 2/10; A61L 2202/11; A61L 2202/14; A61L 2202/16
See application file for complete search history.

(56) References Cited

U.S. PATENT DOCUMENTS

| | | | |
|---|---|---|---|
| 9,352,469 B2 * | 5/2016 | Stewart | .................... B25J 5/007 |
| 10,328,168 B1 | 6/2019 | Veloz et al. | |
| 10,780,189 B2 | 9/2020 | Randers-Pehrson et al. | |
| 10,786,586 B2 | 9/2020 | Igarashi | |
| 2017/0112954 A1 * | 4/2017 | Dayton | ..................... A61L 9/20 |
| 2018/0303134 A1 | 10/2018 | Dobrinsky et al. | |
| 2019/0160192 A1 * | 5/2019 | Fudakowski | ............. A61L 2/26 |
| 2019/0354381 A1 | 11/2019 | Takacs et al. | |

OTHER PUBLICATIONS

Ackerman, E., Autonomous robots are helping kill Coronoavirus in hospitals, Spectrum, Mar. 11, 2020, 4 pages.
Illuminating Engineering Society, IES Committee Report: Germicidal Ultraviolet (GUV)—Frequently Asked Questions, Apr. 15, 2020, 24 pages.

(Continued)

*Primary Examiner* — Sean E Conley
(74) *Attorney, Agent, or Firm* — CHRISTENSEN O'CONNOR JOHNSON KINDNESS PLLC (57) ABSTRACT

A germicidal lighting system may include a directional germicidal light source for emitting a beam of germicidal light. The directional germicidal light may be mounted movably with respect to a structure, which can in turn be movable. The directional germicidal light source may be moved and oriented relative to surfaces to be irradiated using the motion relative to the structure or the motion of the structure. The directional germicidal light source may be moved to scan a surface to smooth out dosage. Dosage may also be controlled using sensors to monitor the dosage applied.

8 Claims, 7 Drawing Sheets

(56) References Cited

OTHER PUBLICATIONS

Miller, S.L., "Upper room germicidal ultraviolet systems for air disinfection are ready for wide implementation," American Journal of Respiratory and Critical Care Medicine, 192(4):407-409, 2015.
Laser Components, Transmission of UV Light with Optical Fiber, Product website, 12 pages, downloaded May 6, 2020.
Wikipedia, Ultraviolet, 29 pages, downloaded May 5, 2020.
Wikipedia, Ultravolet germicidal irradiation, 11 pages, downloaded May 5, 2020.
Verilux, UVC Sanitizing, Product webpage, 2 pages, downloaded May 5, 2020.
Buonanno, M., et al., "Far-UVC light (222 nm) efficiently and safely inactives airborne human coronaviruses," Scientific Reports, 10:1-8, 2018.
Narita, K., et al., "Chronic irradiation with 222-nm UVC light induces neither DNA damage nor epidermal lesions in mouse skin, even at high doses," PLoS One, 13(7):1-9, Jul. 5, 2018.
Narita, K., et al. "Disinfection and healing effects of 222-nm UVC light on methicillin-resistant *Staphylococcus aureus* Infection in mouse wounds," Journal of Photochemistry and Photobiology B: Biology, 178:10-18, 2017.

\* cited by examiner

GERMICIDAL LIGHTING SYSTEM

TECHNICAL FIELD

Germicidal lighting systems.

BACKGROUND

A germicidal lighting system uses ultraviolet radiant energy, for example UVC, to inactivate microorganisms such as bacteria, mold spores, fungi, or viruses (germs). Germicidal effectiveness depends on the exposure dose (radiant exposure, typically in millijoules per square centimeter, $mJ/cm^2$, or joules per square meter, $J/m^2$), which is the product of the dose-rate (irradiance, typically in $mW/cm^2$ or $W/m^2$) and time (from 1 µs to several hours).

Typically, a threshold dose of radiation such as UVC on an area can effectively inactivate the germs on that area. A larger dose of UVC radiation than the threshold may cause or worsen color fade, material damage, or equipment disorder in that area without significantly improving germicidal effect. A smaller dose of UVC radiation than the threshold may not meet the germicidal purpose.

Most commercially available germicidal UVC devices generate diffusing non controllable scattering UVC beams. The UVC doses on the radiated area are not evenly distributed. Some small area may receive overdose of UVC to damage things while another small area may receive not enough dose to effectively kill germs. If there are some objects which can block the UVC beams on the radiated area, shadowed parts of the objects (e.g. the inner parts of the handles of doors) may receive no UVC beams at all.

SUMMARY

Embodiments of this germicidal lighting system solve one or more of the problems mentioned in the background for example by providing directional UVC radiation beams and means to control the beams. In one example, beams may be controlled using mechanical devices such as robotic arms or swingable light fixtures. In a further example, there may be plural swingable light fixtures mounted on a vertical column, which in turn may be rotatable about a longitudinal axis.

Controlled directional beams may be used to provide desired amounts of light to varied surfaces, such as flat and curved surfaces, holes, channels or other regular or irregular subjects. The beams may also provide relative even intensity and provide doses close to a desired amount, which may for example be a germicidal threshold for UVC light shining on the surface of the subject. Embodiments may provide a high efficiency of germicidal tasks, optimize radiation time, and avoid over-exposure of UVC radiation on subjects that may degenerate under UVC light.

The germicidal lighting system may be controlled by an AI (artificial intelligent) control system implemented by software running on a processor incorporated into the germicidal lighting system itself or into device on the UVC lighting system to achieve automatic disinfecting tasks. The UVC lighting system may also be controlled, monitored, or transmit information through wired or wireless methods including with internet, local net, Bluetooth, or internet of things (IoT).

BRIEF DESCRIPTION OF THE FIGURES

Embodiments will now be described with reference to the figures, in which like reference characters denote like elements, by way of example, and in which.

DETAILED DESCRIPTION

Immaterial modifications may be made to the embodiments described here without departing from what is covered by the claims.

Germicidal Lighting System

A germicidal lighting system may include a movable structure, for example a robot, trolley or handcart, on which a germicidal light source is mounted.

Figure 1:
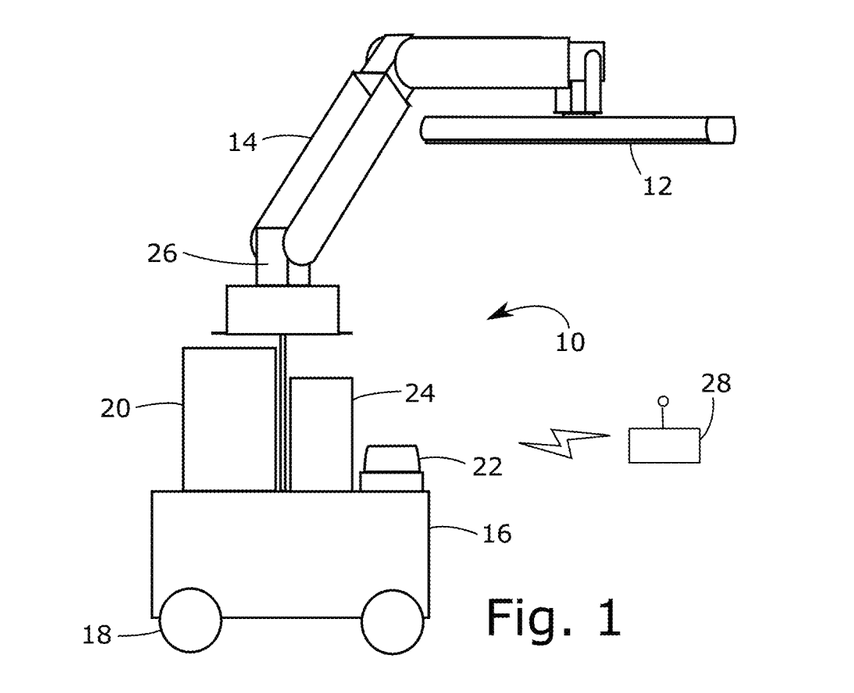
FIG. 1 is a schematic diagram showing an exemplary germicidal lighting system.

FIG. 1 is a schematic diagram showing an example germicidal lighting system 10. In this example, a germicidal light source 12 is mounted on a robot arm 14. The robot arm extends from movable structure 16, in this example having wheels 18. The germicidal light source 12 is shown in more detail in FIGS. 2-3. The light source 12 in this example is a linear shaped light having a direction of extent perpendicular to a direction of light emission. The robot arm 14 may move and orient the light source 12 to adjust the position and direction of light emission. The robot arm may be moved by actuators such as actuator 26 shown in FIG. 1, or may be moved manually.

The germicidal light source 12 may be, for example, a UVC light source. The UVC light source can be gas discharge lamps, LEDs, or lasers in any shapes. A germicidal light source can be a linear light, other special shaped light, or a spotlight. The UVC light source may comprise a single linear lamp as shown in FIG. 1, but could also use a spot lamp, a single lamp of a different shape or multiple lamps, each of which may be a linear or spot lamp or a lamp of a different shape. The mention of an element, such as a germicidal light source, in the singular does not exclude additional similar elements.

The lighting system may be powered by, for example, rechargeable batteries 20 or by mains power. The germicidal light source 12 may be directional. The directional germicidal light source may be mounted movably on the movable structure for adjusting an orientation of the directional germicidal light source relative to the movable structure. For example, in the embodiment shown in FIG. 1 the germicidal light source 12 is mounted on robot arm 14 to control position and direction. In another example, the germicidal light source 12 may be mounted on a rotating mount to control direction only.

The germicidal lighting system may include one or more sensors, shown in FIG. 1 as a sensor and alarm system 22. Where the germicidal lighting system is controlled by a computer, information from the sensors may be sent to the computer for the computer to use in controlling the germicidal lighting system. Regardless of whether the system is computer-controlled, information from the sensors may be used to supply information to users, for example on a display or an alarm. A computer, whether or not controlling the system, may analyze information from the sensors and determine whether to generate an alarm based on the analysis.

An alarm system, for example using light or sound, may be provided, shown in FIG. 1 as a sensor and alarm system 22. For example, an alarm may be generated on the germicidal lighting system producing germicidal light, in order to alert people in the vicinity that such light is being produced. An alarm may also be provided in other circumstances such as on determining that a desired dose has been supplied to a surface. An alarm may be produced in any other circumstances which it is considered desirable to bring to the attention of people, such as for example the sensors have detected a potentially unsafe condition such as a person in a field of emission of the germicidal light. In the event of detecting an unsafe condition, the system may stop the emission of germicidal light immediately and generate the alarm in order to alert people of the need to remedy the unsafe condition or to override the halting of the system in the event that the detection is a false detection.

The germicidal lighting system may be automated and controlled by a computer that may be mounted on the moving structure, such as in a control box 24 as shown in FIG. 1, or located elsewhere. The computer may operate the germicidal lighting system following high-level instructions that may be presented to the computer for example by the means described above.

The germicidal lighting system may be configured with hardware or software to limit the germicidal lighting to selected disinfecting areas. The selections of disinfecting areas could be preprogrammed, for example by mapping and selecting areas for disinfection, or could be remote controlled, or controlled by an artificial intelligent system.

The germicidal lighting system may be self moving, e.g. using a motor, or manually pushed, and the germicidal light source may be moved and adjusted manually or using an actuator. The germicidal light source may be controlled by various means, including commanding from a control panel with push-button or touch screen; commanding from a wired remote controller; commanding from a infra-red remote controller; commanding from smart phones/pads via Bluetooth network; commanding from smart phones/pads via WIFI network; commanding from a computer via WIFI network or Bluetooth network or Ethernet or other wired/wireless network including wired or wireless IoT. The robotic arm and the scannable light fixture can also be controlled by a robot. The robotic arm and the scannable light fixture can be controlled by the combinations of the above controlling methods. FIG. 1 schematically shows a remote controller 28 for controlling the germicidal lighting system.

The light source may be movable in a scanning motion. A scanning motion may include, e.g. translational motion of the light source, for example perpendicular to the direction of extent. A scanning effect may also be achieved by changing the direction of light emission. In an embodiment, the direction of extent of a linear light source may also be rotatable.

Figure 2:
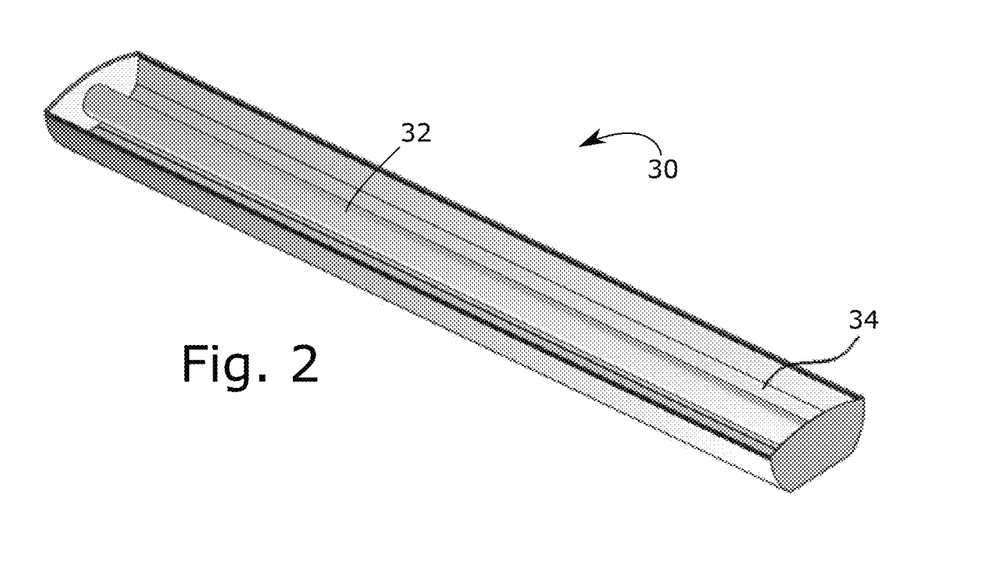
FIG. 2 is an isometric view of an example directional germicidal light source for the germicidal lighting system of FIG. 1.
Figure 3:
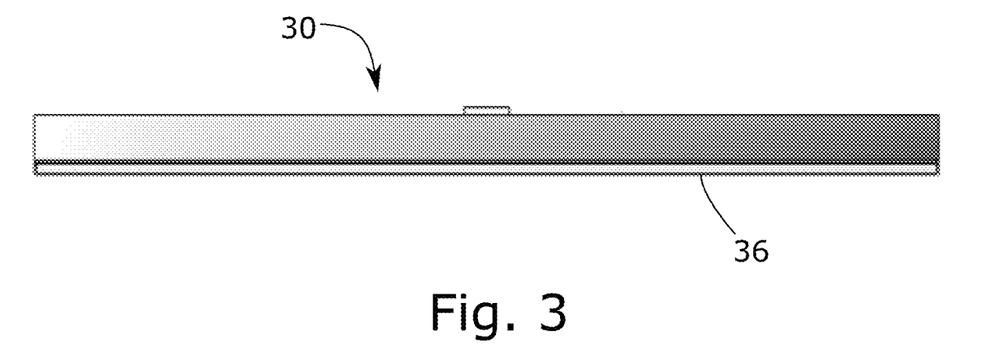
FIG. 3 is a side view of the directional germicidal light source of FIG. 2, also including a lens.
Figure 7:
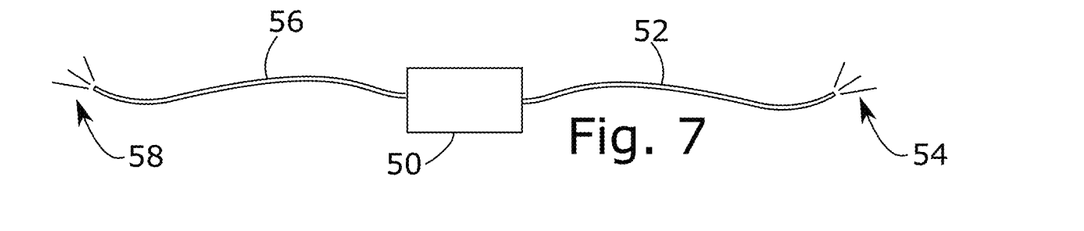
FIG. 7 is a schematic diagram of an example directional germicidal light source using an optical fiber to direct light.

A germicidal light source may include a mirror, a lens or both for directing the light from the germicidal light source. FIG. 2 shows an example light source 30 having a light producing element 32 with a mirror 34, and FIG. 3 shows the light source 30 of FIG. 2 also including a lens 36. A relative position of the lens 36 and the light producing element 32 may be adjustable, for example by moving the light producing element. A germicidal light source could also be directional by producing light in a collimated manner, as in a laser, or by blocking light traveling in unintended directions. Directionality may also be provided by directing the light using a waveguide, such as an optical fiber as shown in FIG. 7 or multiple optical fibers separately or in a bundle. FIG. 7 shows a germicidal light producing element 50 which sends germicidal light into an optical fiber 52. The germicidal light 54 exits from an end of the optical fiber opposite from the light producing element 50. The waveguide may be moved as a whole unit or may be flexible such that an exit of the waveguide may be moved separately from a light producing element, as shown for the optical fiber 52 in FIG. 7. FIG. 7 also shows an optional additional optical fiber 56 directing germicidal light 58.

Figure 4:
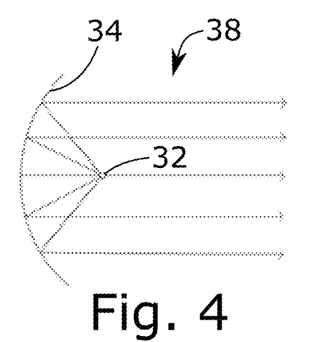
FIG. 4 is a schematic diagram of a germicidal light source including a concave mirror positioned to cause the light source to produce parallel light.
Figure 5:
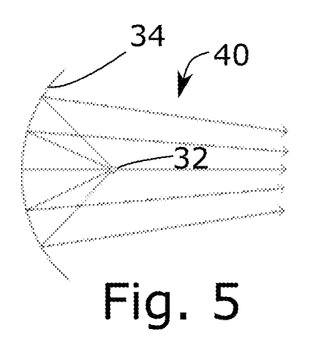
FIG. 5 is a schematic diagram of the germicidal light source of FIG. 4 with the concave mirror moved to cause the light source to produce converging light.
Figure 6:
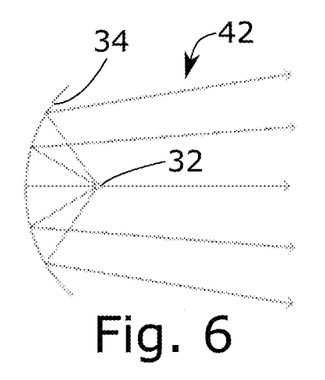
FIG. 6 is a schematic diagram of the germicidal light source of FIG. 4 with the concave mirror moved to cause the light source to produce diverging light.

The position and direction of a directional germicidal light source may be considered to be the position of, and direction of light emitted from, an exit optical element or aperture, regardless of the positioning of the light producing element or any intermediate optical elements. The exit of the additional optical fiber 56 shown in FIG. 7 is positioned and oriented independently of the first optical fiber and thus forms an additional directional germicidal light source. In this case, the different germicidal light sources share the same light producing element 50, but they could also have different respective light producing elements.

Where the directional germicidal light source includes a mirror 34, the mirror can be, for example, a concave mirror. In an embodiment, the relative distance between mirror 34 and light-producing element 32 can be adjusted as shown in FIGS. 4-6. The mirror 34 may be shaped so that, for some relative distance between the mirror and a light producing element 32, the output from the mirror forms a beam of generally parallel light 38, as shown schematically in FIG. 4. In the example shown in FIGS. 4-6, the relative distance between mirror and a light-producing element is increased in FIG. 5 to produce a convergent beam 40, and reduced in FIG. 6 to produce a divergent beam 42. In other embodiments, adjustments in distance could produce varying degrees of convergence or divergence. A convex mirror or a flat mirror could also be used and would produce divergent light regardless of distance.

A lens 36 such as shown in FIG. 3 may also be used to adjust a focus of the directional germicidal light source. In an embodiment a focus of the germicidal light source may be adjusted by adjusting the lens, for example by varying a position of the lens.

In an embodiment, the light may be adjusted in direction by rotating the mirror around the light producing element.

Germicidal Lighting Methods

Figure 8:
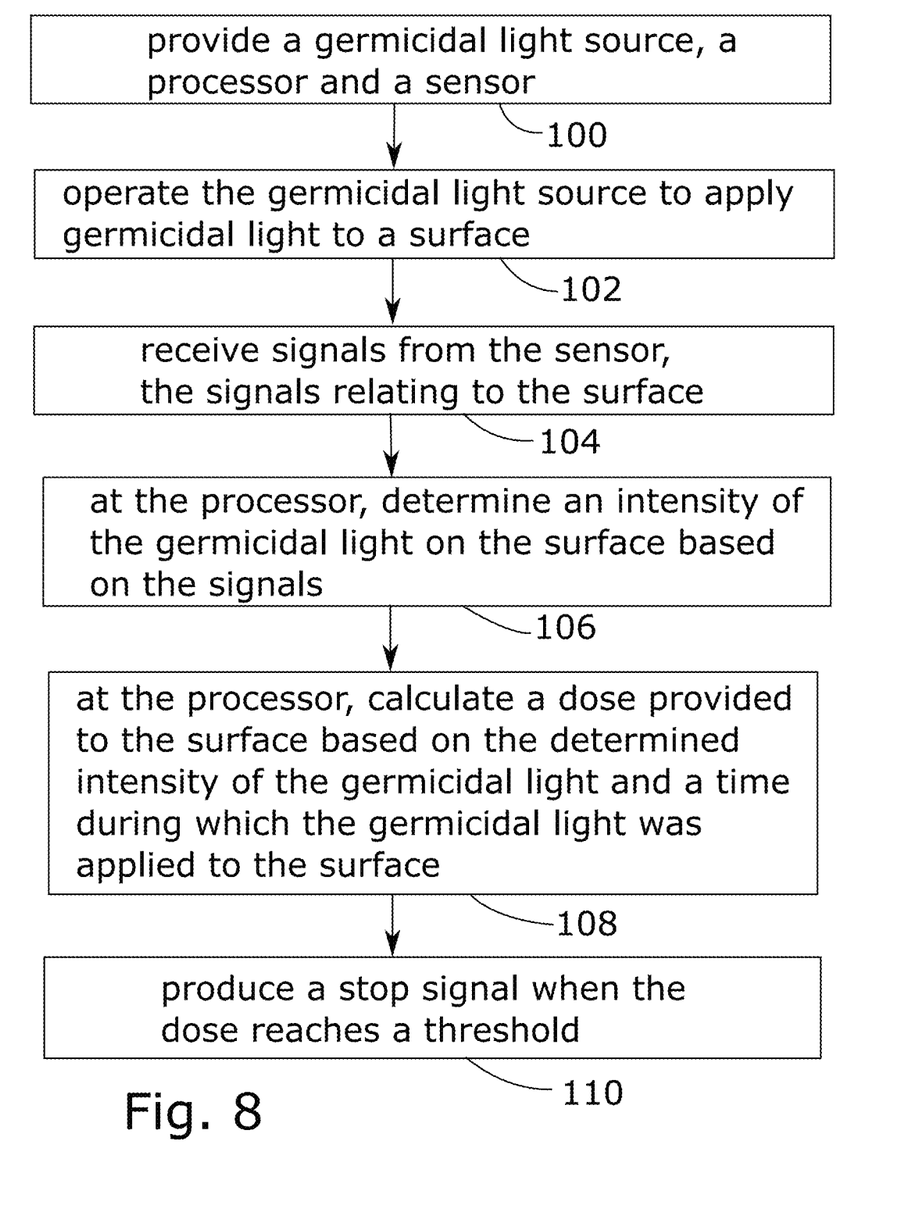
FIG. 8 is a flow chart showing a method of controlling a dose provided to a surface by a germicidal lighting system.

FIG. 8 is a flow chart showing an example method of managing dose when disinfecting using germicidal lighting. In step 100, a germicidal light source is provided in conjunction with a processor and a sensor. The mention of an element in the singular does not exclude others being present, here or in the claims. The germicidal light source may be operated in step 102 to apply germicidal light to a surface, in step 104 the processor receiving signals from the sensor relating to the surface and in step 106 the processor determining an intensity of the germicidal light on the surface based on the signals. The processor may then in step 108 calculate a dose provided to the surface based on the determined intensity of the germicidal light on the surface and a time during which the germicidal light was applied to the surface. The processor may in step 110 produce a stop signal when the dose reaches a threshold. The stop signal can be for example, a signal to the germicidal light source to cause the germicidal light source to turn off. Note, a "signal" can include an absence of an expected signal, for example, the ceasing of providing a signal to the light source to turn off. The germicidal light source may be movable in position or orientation in response to movement signals from the processor, and the stop signal can be a movement signal, causing the germicidal light source to no longer irradiate the same surface. The stop signal can also be an alarm presented to a user, so that the user can cause the germicidal light source to cease to provide germicidal light to the surface, for example by turning off or moving the germicidal light source.

There may be one or more sensors. The one or more sensors may include, for example, video cameras, temperature sensors, humidity sensors, infrared sensors, sound sensors, microwave sensors and lidar. In an embodiment a distance sensor is used. A distance sensor can include any sensor that may send to the processor signals indicative of a distance between the germicidal light source and the surface, including video cameras, infrared sensors, sonar or lidar. The processor may determine the intensity of the germicidal light on the surface based on the signals indicative of the distance between the germicidal light source and the surface. With a distance sensor, the control box can measure the area and the distance of the surface in front of the light fixture which the germicidal light, e.g. UVC, beams radiate. The control box can then calculate the UVC dose needed and control the radiation time so that the radiating UVC dose passes the germ-killing threshold, but does not overdose.

Other uses of sensors include detecting that a surface is being damaged by germicidal light, detecting that germicidal light is not reaching an intended surface, detecting an intensity of germicidal light being reflected from a surface, or detecting that an object or person is present that the system should avoid irradiating with germicidal light.

Sensors may also be used to detect infected or polluted areas to be targeted specifically or exclusively by the germicidal lighting system. Data from one or more sensors may be supplied to a processor to identify infected or polluted areas, for example using AI, or displayed to a human user. The one or more sensors can include video imagery or other sensors.

The germicidal lighting system can disinfect the infected areas according to the directly input commands of a user, following preprogrammed routines in the system, or using AI results or wired or wireless signals from a remote controlling system.

Figure 9:
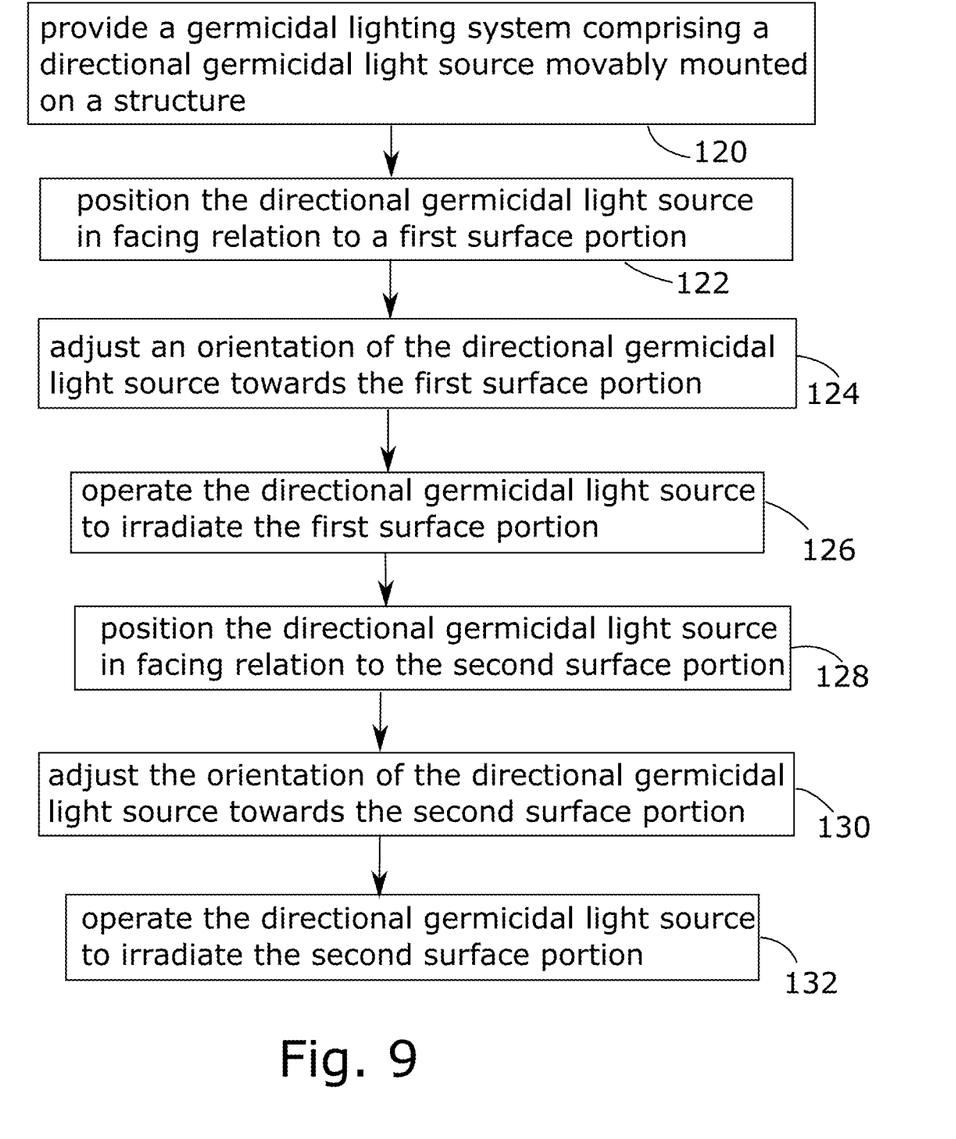
FIG. 9 is a flow chart showing a method of irradiating first and second portions of a surface.

FIG. 9 is a flow chart showing a method of disinfection of a surface. In step 120 a germicidal lighting system is provided comprising a directional germicidal light source movably mounted on a structure. The structure may be, for example, a movable structure. The germicidal lighting system may be a germicidal lighting system as described above. The germicidal lighting system may be used to sequentially irradiate a first surface portion and then a second surface portion. For example, as shown in FIG. 9, the germicidal lighting system may irradiate the first surface by in step 122 positioning the directional germicidal light source in facing relation to a first surface, e.g. so that the first surface generally faces the germicidal lighting system, in step 124 adjusting an orientation of the directional germicidal light source towards the first surface portion, and in step 126 operating the directional germicidal light source to irradiate the first surface portion. The germicidal lighting system may irradiate the second surface portion by in step 128 positioning the directional germicidal light source in facing relation to the second surface portion, in step 130 adjusting the orientation of the directional germicidal light source towards the second surface portion; and in step 132 operating the germicidal light source to irradiate the second surface portion.

Where the structure is a movable structure, the step 128 of positioning the directional germicidal light source in facing relation to the second surface portion may comprise moving the movable structure. Regardless of whether the structure is movable, this step may comprise adjusting a position of the directional germicidal light source relative to the structure.

Where the structure is a movable structure, the step 130 of adjusting the orientation of the directional germicidal light source towards the second surface portion may comprise moving the movable structure. Regardless of whether the structure is movable, this step may comprise adjusting the orientation of the directional germicidal light source relative to the structure.

The directional germicidal light source may remain active between the steps of operating the directional germicidal light source to irradiate the first surface portion and operating the directional germicidal light source to irradiate the second surface portion. This allows smoothing of the average light intensity over time as a field of irradiation of the germicidal light source moves over any given point on surfaces to be irradiated.

In an embodiment, the first surface portion and the second surface portion may form parts of a scanned surface. The directional germicidal lighting system sequentially irradiates different portions of the scanned surface, which may occur for example in a series of discrete steps or in one continuous motion.

In an example, a robot arm moves the directional germicidal light across the surface, and as the robot arm moves, the directional germicidal light source rotates relative to the robot arm to keep the directional germicidal light source directed substantially perpendicularly to the surface.

If a linear germicidal light source is substantially uniform in brightness along its length, but non-uniform perpendicular to its length, e.g. by more brightly illuminating a central line of focus and less brightly illuminating away from the line, then the above method of scanning makes the applied dose more uniform by applying the different brightness levels over time to each point on the surface.

Non-uniformity perpendicular to the direction of scanning can also be smoothed by moving the field of illumination of the germicidal light source on a path forming substantially parallel lines during the scanning, the substantially parallel lines overlapping. For example, if a light source forms a spotlight with greater illumination in the center, overlapping subsequent passes can result in smoother application of the dose. Even a highly irregular field of illumination could be smoothed by many closely overlapping passes.

Multiple germicidal light sources may also be used to smooth the application of the dose of germicidal light. By orienting the different germicidal light sources separately, they can have similar cumulative effect as a single germicidal light source at different positions at different times. The multiple sources can reduce the total amount of motion needed to achieve a given amount of smoothing, relative to a single germicidal light source.

The speed and path of the scanning may also be adjusted to control the dose. For example, where different portions of a surface are at different distances, the light may be moved slower when directed at more distant portions of the surface. The processor may also monitor the dose provided, and adjust the path of scanning to avoid further illuminating portions that have already received the desired dose.

A higher dose may also be applied to surfaces for which disinfection is particularly important or which are likely to be able to withstand higher levels of radiation. For example, a higher dose may be applied to doorknobs than walls.

As described above, a directional germicidal light may have adjustable focus by adjusting the distance between a light source and a mirror, or by adjusting a lens in front of the light fixture. This changes the lighting area, hence the exposure time.

Some special objects on the radiated surface, such as the handles of the doors, can be scanned by moving the light fixture to each side of the object, and be directionally radiated with divergent beams so that inner portions of the object can receive enough UVC radiation. The divergent beams can spread the light across portions of the object that may be difficult to reliably irradiate with focused beams. A divergent focus may be useful to illuminate a nearby surface with higher intensity than a more distant surface. For example, a divergent beam may illuminate the doorknob more strongly than more distance surfaces across the room. A highly convergent beam may also be used, as it becomes divergent beyond a distance of focus of the convergent beam.

Focus may also be adjusted for example depending on the apparent size of a surface to be disinfected or to be avoided. For example, focus may be adjusted to avoid overexposing a sensitive surface. Nearby surfaces may be disinfected with tighter focus to avoid spillage onto the sensitive surface.

Figure 10:
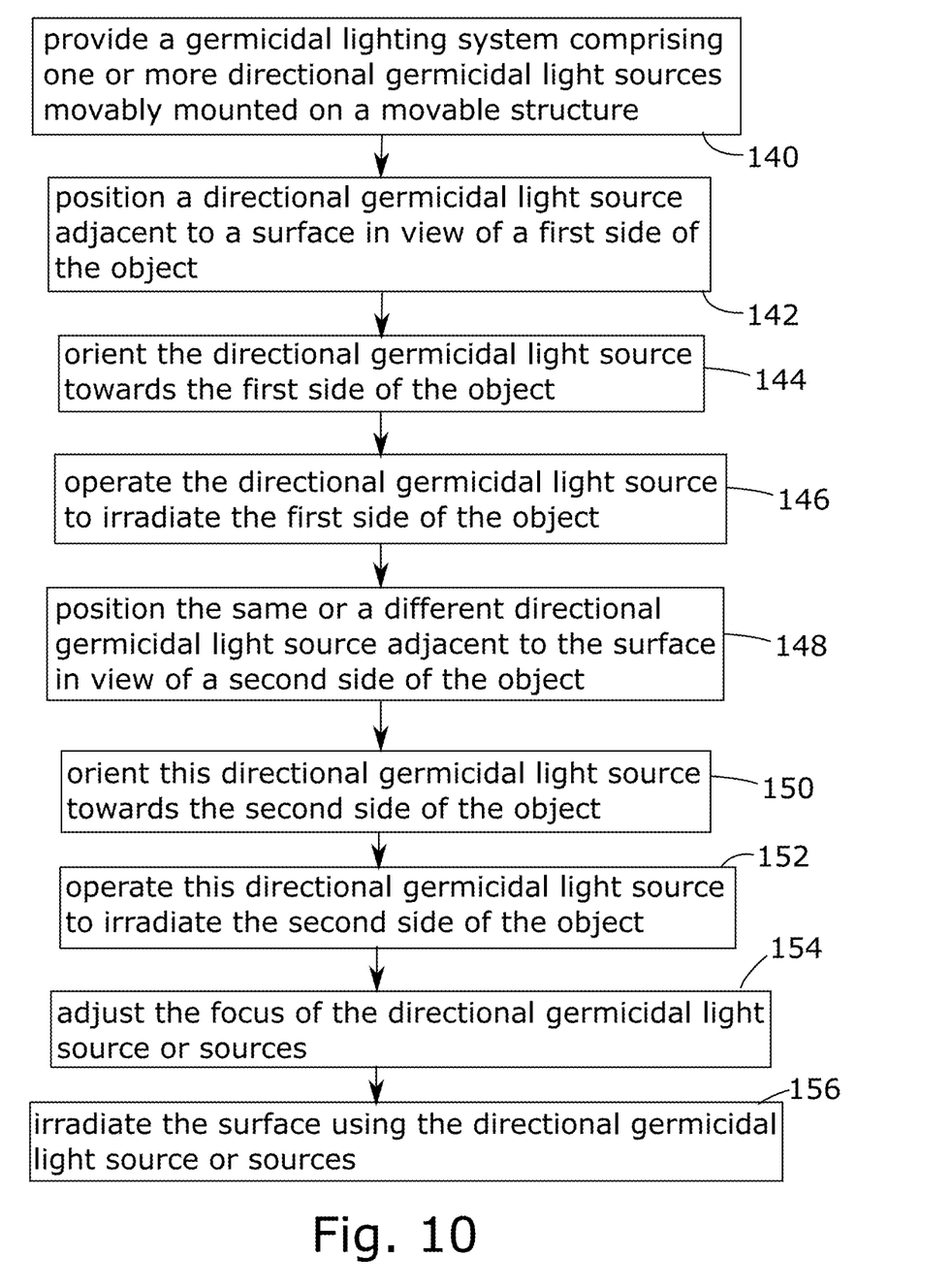
FIG. 10 is a flow chart showing a method of irradiating an object adjacent to a surface.

FIG. 10 is a flow chart showing a method of irradiation of an object. In step 140, a germicidal lighting system is provided, which may have one or more directional germicidal light sources movably mounted on a movable structure. In step 142, a directional germicidal light source is positioned adjacent to the surface in view of a first side of the object. In step 144, the directional germicidal light source is oriented towards the first side of the object and in step 146 the directional germicidal light source is operated to irradiate the first side of the object. In step 148, a directional germicidal light source is positioned adjacent to the surface in view of the second side of the object. This may be the same directional germicidal light source used to irradiate the first side of the object, or a different directional germicidal light source. In step 150, this directional germicidal light source is oriented towards the second side of the object, and in step 152 this directional germicidal light source is operated to irradiate the second side of the object. The surface may also be irradiated in step 156 using the directional germicidal light source or sources. Optionally, in step 154 the focus of the directional germicidal light source or sources may be adjusted between irradiating the first and second sides of the object and irradiating the surface.

A germicidal lighting system may also scan a surface without changing the position of the directional germicidal light source. In an example, the directional germicidal light source has a linear extent as shown in FIG. 1, and the scanning comprises rotating the direction of light emission while keeping the direction of linear extent the same. For example, where the directional germicidal light source includes a mirror as shown in FIGS. 2-6, the direction of light emission may be rotated by rotating the mirror 34 around the light producing element 32.

The germicidal lighting system may be applied to deactivate human pathogens, for example in a hospital, or may be used in other contexts such as horticultural.

Figure 11:
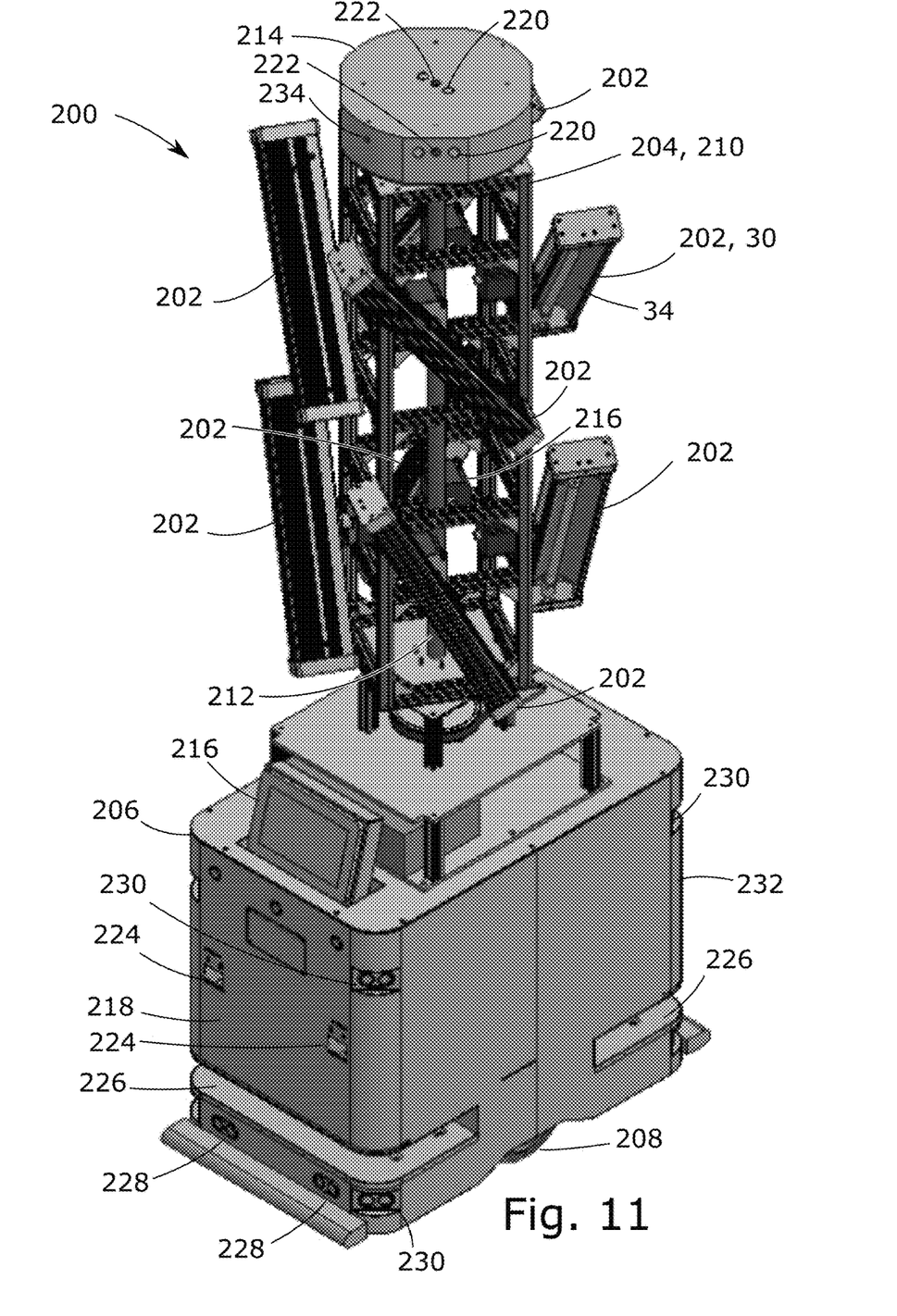
FIG. 11 is an isometric view of a germicidal lighting system with multiple light sources around a mast on a movable base.

FIG. 11 shows a germicidal lighting system 200 with multiple directional germicidal light sources 202 supported by a tower 204 mounted on a base 206. The base 206 may be movable using, for example, wheels 208. The tower 204 in the embodiment shown comprises a rotating structure 210 that rotates around a column 212 fixed to the base 206. This may allow 360 degree horizontal rotation of the lights around the axis defined by the column. In this embodiment, a header 214 is fixed to the top of the column 212. Each light source 202 may be directional, for example a directional germicidal light source 30 including a mirror 34 as shown in FIGS. 2-6. For example, it may be configured to direct light in parallel manner as shown in FIG. 4. Any configuration or variant of directional germicidal light source disclosed in this document may also be used. In the embodiment shown in FIG. 11, there are eight directional germicidal light sources arranged in two tiers each having one light source 202 at each of four sides of the rotatable structure. Each directional germicidal light source 202 shown is supported on a respective shaft 216 extending from the rotational structure and is rotatable around an axis longitudinal to the shaft 216. In the embodiment shown, the shaft 216 is oriented horizontally and the directional germicidal light sources extend substantially perpendicularly to the shaft, with the direction of light oriented substantially perpendicularly to both the shaft and the light source, so that the rotation occurs in the manner of the hands of a clock. The rotation may be caused by an actuator (not shown) controlled by a processor within the germicidal lighting system 200, or by any other means disclosed in this document. This rotation may be up to, in this embodiment, 45 degrees in either rotational direction from a position where the directional lights are vertically oriented, and direct light substantially horizontally. This allows the light to be directed upwards or downwards in a 90 degree range of angles. In other embodiments, the lights may have greater range of motion, for example to face down, up or other directions. The robot may rotate the structure 210 at the same time as rotating the light sources relative to the structure.

The base 206 may contain a battery (not shown). Any other means of powering the germicidal lighting system disclosed in this document may also be used. The germicidal lighting system 200 may include a processor at any suitable location, in an example within the header 214. The germicidal lighting system 200 may also, in this or any other embodiment of a germicidal lighting system including computer control, operate autonomously. The germicidal lighting system 200 may also include a control panel 216. The autonomous operation may use a suite of sensors included in the robot.

Figure 12:
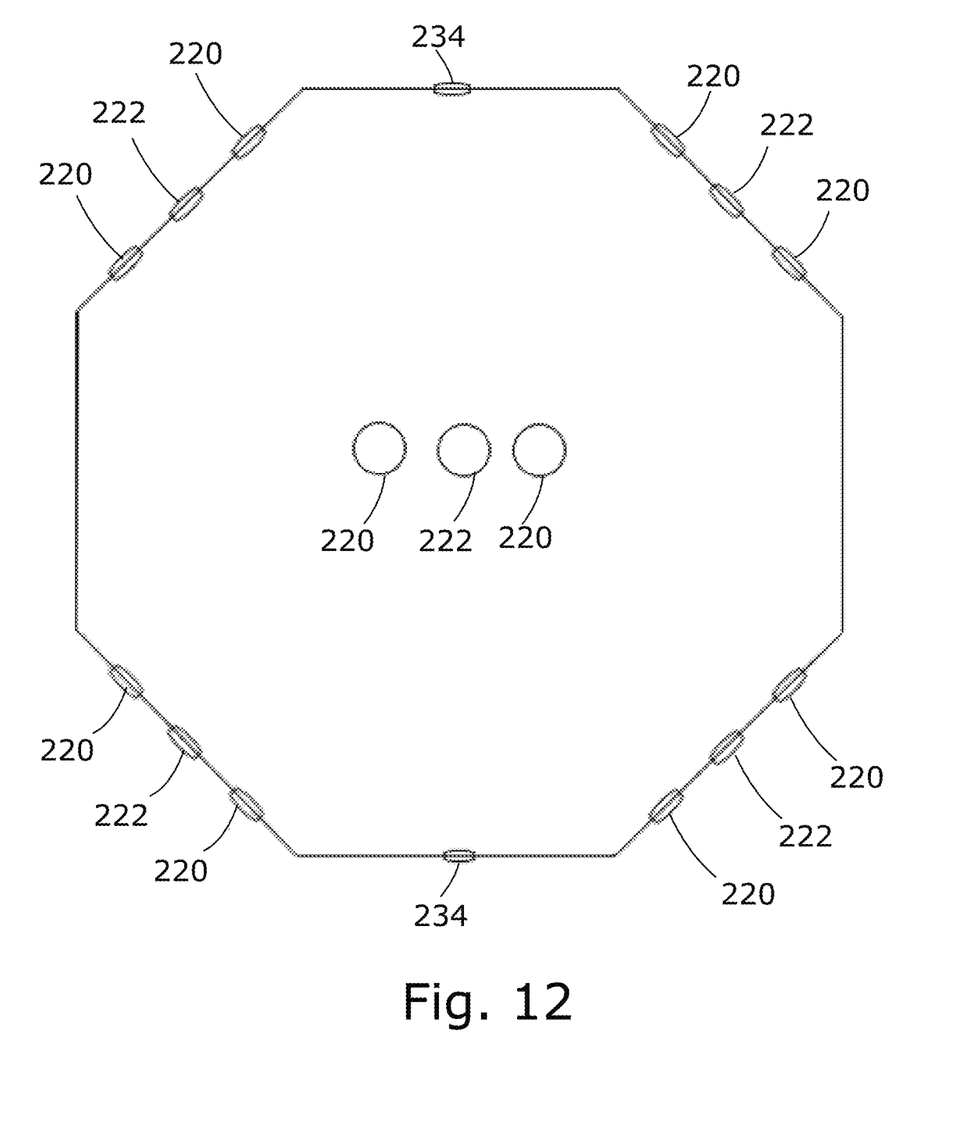
FIG. 12 is a top view of a header for a germicidal lighting system as shown in FIG. 11, with an exemplary arrangement of sensors shown.

An example suite of sensors is described in relation to the embodiment of FIG. 11. The arrangement of the sensors on the header 214 is shown schematically in FIG. 12, which shows a top view with the upward direction on the page corresponding to a frontward direction for the robot. In this example, the header 214 includes five pairs of video cameras 220, four arranged at corners of the header and one at the top of the header for stereo vision in all directions. The header also includes here five passive infrared (PIR) sensors 222, four arranged on the respective vertical surfaces of an octagonal prism forming the header and one on top of the header. These sensors may be used to detect the presence of humans. There may also be two optical sensors 234, one at the front and one at the back. The optical sensors are used to avoid collisions with obstacles. The optical sensors send out and detect infrared light. The optical sensors can be used to detect obstacles in 3D space, and measure the distance to the obstacle. Optical sensors are typically cheaper than cameras. In some embodiments, the optical sensors can be used to detect and measure characteristics of obstacles on their own, rather than a processor receiving raw sensor data and detecting the obstacle and determining its characteristics. The video cameras may be used for example to check the environment for humans and measure the positions of, distance to and trend of motion of the humans, and the video cameras and optical sensors may be used separately or together to avoid collision with the top of the robot. This embodiment also includes four cameras 224 mounted on the base 206, including two cameras at the front 218 of the base 206 and two cameras at the rear for depth perception in front and rear directions for 3D navigation. The embodiment also includes Lidar sensors mounted in cavities 226, one at the front and one at the back of the base 206, to provide 2D navigation. This embodiment also includes four ultrasonic sensors 228 in the base, again two at the front and two at the rear, to detect obstacles. Eight optical sensors 230, two on each corner surface 232 of the base 206, are used to avoid collisions with obstacles. All sensors may be provided in a symmetric arrangement (front and back) to enable the robot to move in both directions equally well.

This embodiment or any other embodiment of a germicidal lighting system may be used with germicidal light in a range of wavelengths selected to cause reduced harm to humans, for example at or near 222 nm.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A germicidal lighting system comprising:
    a movable structure including a tower and a base, and a column fixed to the base, the tower being rotatable around the column about an axis defined by the column, the axis being substantially vertical relative to the base;
    a header mounted on top of the column, the header including one or more video cameras;
    a shaft mounted to the tower; and;
    a directional germicidal light source mounted to the movable structure via the shaft;
    the directional germicidal light source being rotatable about an axis defined by the shaft for adjusting an orientation of the directional germicidal light source relative to the movable structure.

2. The germicidal lighting system of claim 1 in which the directional germicidal light source is manually rotatable about the axis to adjust the orientation of the directional germicidal light source relative to the movable structure.

3. The germicidal lighting system of claim 1 in which the directional germicidal light source is rotatable about the axis using an actuator to adjust the orientation of the directional germicidal light source relative to the movable structure.

4. The germicidal lighting system of claim 1 configured to be controlled via remote control.

5. The germicidal lighting system of claim 4 configured to be controlled by wireless control.

6. The germicidal lighting system of claim 4 configured to be controlled by a user interface over remote control.

7. The germicidal lighting system of claim 1 in which the directional germicidal light source comprises a concave or convex mirror configured to direct light from the directional germicidal light source.

8. The germicidal lighting system of claim 1 further comprising a battery for supplying power to the germicidal lighting system.

* * * * *

UNITED STATES PATENT AND TRADEMARK OFFICE
CERTIFICATE OF CORRECTION

PATENT NO. : 12,194,170 B2  
APPLICATION NO. : 17/313983  
DATED : January 14, 2025  
INVENTOR(S) : Xinxin Shan Page 1 of 1

It is certified that error appears in the above-identified patent and that said Letters Patent is hereby corrected as shown below:

In the Claims

| Column | Line | |
|---|---|---|
| 10 | 19 | Claim 1, delete "and ;" and insert -- and -- |

Signed and Sealed this  
Twenty-second Day of April, 2025

Coke Morgan Stewart  
*Acting Director of the United States Patent and Trademark Office*